United States Patent
McCullen et al.

(10) Patent No.: US 10,034,755 B2
(45) Date of Patent: Jul. 31, 2018

(54) ANATOMICALLY DESIGNED MENISCUS IMPLANTABLE DEVICES

(71) Applicants: Seth McCullen, Greenville, SC (US); Mario Alberto Accardi, London (GB)

(72) Inventors: Seth McCullen, Greenville, SC (US); Mario Alberto Accardi, London (GB)

( * ) Notice: Subject to any disclaimer, the term of this patent is extended or adjusted under 35 U.S.C. 154(b) by 0 days.

(21) Appl. No.: 15/514,597

(22) PCT Filed: Oct. 2, 2015

(86) PCT No.: PCT/US2015/053630
§ 371 (c)(1),
(2) Date: Mar. 27, 2017

(87) PCT Pub. No.: WO2016/054463
PCT Pub. Date: Apr. 7, 2016

(65) Prior Publication Data
US 2017/0224498 A1     Aug. 10, 2017

Related U.S. Application Data

(60) Provisional application No. 62/058,688, filed on Oct. 2, 2014.

(51) Int. Cl.
*A61F 2/38*     (2006.01)
*A61F 2/30*     (2006.01)

(52) U.S. Cl.
CPC ........ *A61F 2/3872* (2013.01); *A61F 2/30767* (2013.01); *A61F 2002/30009* (2013.01);
(Continued)

(58) Field of Classification Search
CPC ...... A61F 2/3872; A61F 2/3877; A61F 2/389; A61F 2002/3895; A61F 2/30749;
(Continued)

(56) References Cited

U.S. PATENT DOCUMENTS

| | | |
|---|---|---|
| 3,867,728 A | 2/1975 | Stubstad et al. |
| 4,195,368 A | 4/1980 | Patrichi |

(Continued)

FOREIGN PATENT DOCUMENTS

| | | |
|---|---|---|
| EP | 0 372 811 A1 | 6/1990 |
| WO | 2012159018 A1 | 11/2012 |

OTHER PUBLICATIONS

International Search Report and Written Opinion for PCT/US2015/053630, dated Apr. 13, 2017 (8 pages).
(Continued)

*Primary Examiner* — Alvin Stewart
(74) *Attorney, Agent, or Firm* — Thrive IP®; Jeremy M. Stipkala

(57) ABSTRACT

An implant device used to replace and restore the function of the knee meniscus in a human. The compliant, yet resilient device is comprised of a biocompatible, non-degradable three-dimensional body comprised of at least a central body, a second structure, a third structure, and a coating. The device is concentrically aligned wherein the second structure is adjoined to the central body wherein the third structure is adjoined on the central body opposite of the second structure. The third structure further features a first and a second pulling element which is coupled to the central body and forms the outer periphery and major circumference of the device. The device is comprised of multiple components which provide tensile strength, compressive resilience, and attachment mechanisms for replacing the meniscus. Each structure is comprised of multiple surfaces which are further reinforced, separated, and connected by an individual plurality of vertical elements. The implantable device further features a surface coating on the surface of the central body.

21 Claims, 7 Drawing Sheets

(52) U.S. Cl.
CPC .............. *A61F 2002/30014* (2013.01); *A61F 2002/30576* (2013.01)

(58) Field of Classification Search
CPC .. A61F 2002/30751; A61F 2002/30754; A61F 2/30756; A61F 2002/30761; A61F 2002/30764; A61F 2002/30766; A61L 27/52; A61B 17/562
See application file for complete search history.

(56) References Cited

U.S. PATENT DOCUMENTS

| | | | |
|---|---|---|---|
| 4,668,233 A | 5/1987 | Seedhom et al. | |
| 4,919,667 A * | 4/1990 | Richmond | A61F 2/3872 623/14.12 |
| 4,919,677 A | 4/1990 | Richmond | |
| 5,116,357 A | 5/1992 | Eberbach | |
| 5,254,133 A | 10/1993 | Seid | |
| 6,093,205 A | 7/2000 | McLeod et al. | |
| 6,113,623 A * | 9/2000 | Sgro | A61B 17/0057 606/151 |
| 6,113,640 A | 9/2000 | Tormala et al. | |
| 6,645,211 B2 | 11/2003 | Magana | |
| 6,679,914 B1 * | 1/2004 | Gabbay | A61F 2/3872 623/11.11 |
| 6,730,252 B1 | 5/2004 | Teoh et al. | |
| 6,736,854 B2 | 5/2004 | Vadurro et al. | |
| 6,746,485 B1 | 6/2004 | Zucherman et al. | |
| 6,755,867 B2 | 6/2004 | Rousseau | |
| 6,783,546 B2 | 8/2004 | Zucherman et al. | |
| 7,153,325 B2 | 12/2006 | Kim et al. | |
| 7,163,563 B2 * | 1/2007 | Schwartz | A61B 17/064 623/14.12 |
| 7,192,604 B2 | 3/2007 | Brown et al. | |
| 7,429,270 B2 | 9/2008 | Baumgartner | |
| 7,476,250 B1 | 1/2009 | Mansmann | |
| 7,572,291 B2 | 8/2009 | Gil et al. | |
| 7,758,643 B2 | 7/2010 | Stone et al. | |
| 7,871,440 B2 | 1/2011 | Schwartz et al. | |
| 7,905,922 B2 | 3/2011 | Bergeron | |
| 8,282,681 B2 | 10/2012 | McLeod et al. | |
| 8,298,290 B2 | 10/2012 | Pelissier et al. | |
| 8,403,985 B2 | 3/2013 | Hodorek | |
| 8,623,085 B2 * | 1/2014 | Gatt | A61F 2/30756 623/14.12 |
| 8,690,919 B2 | 4/2014 | Lange et al. | |
| 8,771,353 B2 * | 7/2014 | Gedet | A61F 2/3872 623/14.12 |
| 8,858,632 B2 | 10/2014 | Mansmann et al. | |
| 8,968,419 B2 | 3/2015 | Calvez et al. | |
| 8,986,380 B2 * | 3/2015 | Kaplan | A61L 27/3604 623/14.12 |
| 9,005,308 B2 | 4/2015 | Stopek et al. | |
| 9,044,278 B2 | 6/2015 | Tanaka | |
| 9,119,698 B2 | 9/2015 | Bellon Caneiro et al. | |
| 9,211,362 B2 | 12/2015 | Hwang et al. | |
| 9,314,339 B2 * | 4/2016 | Mansmann | A61F 2/30756 |
| 9,498,335 B2 | 11/2016 | McCullen | |
| 2002/0022884 A1 | 2/2002 | Mansmann | |
| 2002/0173855 A1 | 11/2002 | Mansmann | |
| 2003/0036797 A1 | 2/2003 | Malaviya et al. | |
| 2003/0114552 A1 | 6/2003 | Schacht | |
| 2003/0135209 A1 | 7/2003 | Seedhom et al. | |
| 2004/0059416 A1 * | 3/2004 | Murray | A61L 24/043 623/13.15 |
| 2004/0133275 A1 * | 7/2004 | Mansmann | A61F 2/30756 623/14.12 |
| 2004/0143344 A1 | 7/2004 | Malaviya et al. | |
| 2004/0266000 A1 | 12/2004 | Offermann et al. | |
| 2004/0267362 A1 | 12/2004 | Hwang et al. | |
| 2005/0027364 A1 * | 2/2005 | Kim | A61F 2/4425 623/17.13 |
| 2006/0085080 A1 | 4/2006 | Bechgaard et al. | |
| 2006/0241756 A1 * | 10/2006 | Fritz | A61F 2/30756 623/14.12 |
| 2007/0073394 A1 | 3/2007 | Seedhom et al. | |
| 2007/0100450 A1 | 5/2007 | Hodorek | |
| 2007/0239277 A1 | 10/2007 | Beger et al. | |
| 2008/0154370 A1 * | 6/2008 | Mathies | A61F 2/30756 623/14.12 |
| 2008/0183292 A1 | 7/2008 | Trieu | |
| 2009/0087469 A1 | 4/2009 | Zhang et al. | |
| 2009/0132047 A1 * | 5/2009 | Mansmann | A61F 2/0811 623/14.12 |
| 2009/0164014 A1 | 6/2009 | Liljensten et al. | |
| 2009/0276057 A1 | 11/2009 | Trabucco et al. | |
| 2010/0151114 A1 | 6/2010 | Parrott | |
| 2010/0222882 A1 | 9/2010 | Badylak et al. | |
| 2010/0331979 A1 * | 12/2010 | McDade | A61F 2/28 623/14.12 |
| 2011/0066243 A1 | 3/2011 | Rivin et al. | |
| 2011/0282451 A1 | 11/2011 | Sporring | |
| 2012/0045651 A1 | 2/2012 | Myung et al. | |
| 2012/0232656 A1 | 9/2012 | Gedet et al. | |
| 2013/0030528 A1 | 1/2013 | Chen et al. | |
| 2013/0079877 A1 * | 3/2013 | Buma | A61F 2/3872 623/14.12 |
| 2013/0138211 A1 | 5/2013 | Myung et al. | |
| 2013/0172999 A1 * | 7/2013 | Kaplan | A61L 27/3604 623/14.12 |
| 2013/0190873 A1 * | 7/2013 | Mansmann | A61F 2/3872 623/14.12 |
| 2013/0268074 A1 * | 10/2013 | Vowles | A61F 2/3872 623/14.12 |
| 2013/0312897 A1 * | 11/2013 | Vowles | A61B 17/0401 156/83 |
| 2014/0031933 A1 * | 1/2014 | Gatt | A61F 2/30756 623/14.12 |
| 2014/0114426 A1 * | 4/2014 | Forsell | A61F 2/3859 623/20.16 |
| 2014/0222149 A1 * | 8/2014 | Amis | A61F 2/3872 623/14.12 |
| 2014/0277569 A1 | 9/2014 | Lange | |
| 2014/0309739 A1 | 10/2014 | Badylak et al. | |
| 2015/0238318 A1 * | 8/2015 | McCullen | A61F 2/30756 623/14.12 |
| 2016/0256285 A1 * | 9/2016 | Jansen | A61L 27/18 |
| 2017/0065422 A1 * | 3/2017 | McCullen | A61F 2/30756 |
| 2017/0252174 A1 * | 9/2017 | Fox | A61F 2/3872 |

OTHER PUBLICATIONS

Written Opinion for PCT/US2013/062809 dated Jan. 10, 2014 (16 pages).
International Search Report for PCT/US2013/062809 dated Jan. 10, 2014 (4 pages).
Communication and European Search Report, for European Patent Application No. EP 13844365.0, dated May 2, 2016 (8 pages).
U. Klinge et al., "Modified Mesh for Hernia Repair that is Adapted to the Physiology of the Abdominal Wall," Eur. J. Surg. 164 (1998) 951-960.
T. Forstemann et al., "Forces and deformations of the abdominal wall—A mechanical and geometrical approach to the linea alba," J. Biomechanics 44 (2011) 600-606.
K. Junge et al., "Elasticity of the anterior abdominal wall and impact for reparation of incisional hernias using mesh implants," Hernia 5 (2001) 113-118.
W. S. Cobb et al., "Normal Intraabdominal Pressure in Healthy Adults," J. Surg. Res., 129 (2005) 231-235.
M. Smietanski et al., "Biomechanics of the front abdominal wall as a potential factor leading to recurrence with laparoscopic ventral hernia repair," Surg. Endosc. (Published online Dec. 15, 2011).
A. K. Williamson et al., "Compressive properties and function-composition relationships of developing bovine articular cartilage," J. Orthopaedic Res. 19 (2001) 1113-1121.
A. K. Williamson et al., "Tensile mechanical properties of bovine articular cartilage: variations with growth and relationships to collagen network components," J. Orthopaedic Res., 21 (2003) 872-880.

(56) References Cited

OTHER PUBLICATIONS

P. P. Pott et al., "Mechanical Properties of Mesh Materials Used for Hernia Repair and Soft Tissue Augmentation," PLOS One vol. 7, Issue 10 (2012) e46978.
International Search Report and Written Opinion for PCT/US2015/053630 dated Jan. 11, 2016 (10 pages).
European Search Report for PCT/US2015/053630, dated May 16, 2018 (7 pages).

* cited by examiner

ANATOMICALLY DESIGNED MENISCUS IMPLANTABLE DEVICES

CROSS REFERENCE TO RELATED APPLICATIONS

This application represents the National Phase under 35 U.S.C. § 371 of International Patent Application No. PCT/US2015/053630, filed on Oct. 2, 2015, entitled, "ANATOMICALLY DESIGNED MENISCUS IMPLANTABLE DEVICES," and claims benefit of priority to U.S. Provisional Patent Application No. 62/058,688, entitled, "ANATOMICALLY DESIGNED MENISCUS IMPLANT," filed on Oct. 2, 2014, which international application and provisional application are incorporated herein by reference in their entirety.

FIELD OF THE INVENTION

The present invention relates generally to implantable devices and related methods of manufacture and use, and more particularly, to implantable devices having particular application for repairing, replacing, and/or reinforcing an anatomical defect such as a meniscus.

BACKGROUND OF THE INVENTION

The meniscus is a crescent-shaped fibrocartilage tissue paired in both the medial and lateral compartments of the knee between the femur and the tibia. Macroscopically, the menisci are C-shaped (semi-lunar) tissues which feature a triangular (wedge shaped) cross-section and cover and separate the tibial plateau from the femoral condyles providing a bearing surface within the joint. The meniscus plays a critical role in load transmission, stability and in reducing contact stresses in the knee joint which is attributed to the unique shape and microstructure of the tissue. The microstructure of the meniscus is largely comprised of type I collagen fibers and the spatial orientation of these collagen fibers are highly functionalized in order to provide the meniscus' unique mechanical properties. Specifically, the meniscus features circumferential bundles of collagen fibers embedded within a hydrated matrix which acts to bear circumferential hoop stresses. When the meniscus is axially loaded, the meniscus tends to displace radially out of the joint center due to its wedge shaped cross-section. Extrusion is, however, resisted as the meniscus is anchored both posteriorly and anteriorly in the tibia via the meniscal horns, The circumferential arrangement of type I collagen fibers throughout the meniscus as well as the meniscal horns give rise to circumferential, or hoop, stresses which resist radial displacement. The meniscus thus converts vertical load into hoop stresses, thereby reducing contact stresses a mechanism known as the 'hoop stress mechanism'.

Injuries to the meniscus are the most common injuries requiring surgical intervention in orthopaedic practice with approximately one million surgeries occurring in the United States every year. Traumatic tears occur in young, active individuals and are more common in the medial meniscus, usually as a result of rotational forces applied to a flexed knee, while degenerative meniscal tears tend to occur in middle aged and older individuals, as a result of the weakening of the tissue and hence the reduction in mechanical properties.

With increased meniscal injuries, meniscal repair has become a standard procedure, and the traditional treatment of partial or full resection which was previously identified as the gold standard, is now understood to have deleterious effects and should be performed as sparingly as possible. Replacement of the damaged meniscal tissue with an implant aims to restore the knee biomechanics and might avoid articular cartilage degeneration and the onset of osteoarthritis. Different types of meniscal substitutes, such as allografts, collagen based materials, and synthetic biodegradable scaffolds, have been used in experimental and clinical studies. Allograft menisci suffer from problems relating to availability, size matching, cost, and risk of disease transmission. Additionally both allografts and collagen scaffolds experience remodeling after implantation causing shrinkage and reduced mechanical strength. Synthetic biodegradable scaffolds lack durability under knee loading conditions and also vary in the body response to the implant and the quality of the tissue formed. Synthetic biodegradable scaffolds also require the native tissue to be present (typically as a rim) for not only attachment but also as source of autologous cells which can seed the implant. Mimicking the microstructure and mechanical property distribution of the meniscus improves the chances for restoring the contact pressures along the tibial plateau during normal activities, and preventing the onset of osteoarthritis following injury. Accordingly, an improved anatomically designed meniscus implantable device is needed to replicate the mechanical properties distribution within the native meniscus.

Prosthetic meniscus implants are a novel treatment method to repair meniscal lesions. To date, there is no meniscus substitute that takes into account the microstructure of the native meniscus. Implantable devices that can restore and replace the function of the meniscus would be of great interest for orthopaedic applications given the clear indication of the unmet need in the area. The challenge in developing a meniscal replacement with biomechanical characteristics close to that of the native meniscus lies in the construction and design choice of material. Accordingly, it is an object of the present invention to provide an improved implantable device for treating meniscal injuries through replacement with an anatomically designed meniscus implant.

SUMMARY OF THE INVENTION

There is a need for an anatomically designed meniscus implant device. The present invention provides an implantable device for repairing, replacing, or reinforcing a meniscus comprising a three-dimensional biocompatible non-degradable structure. The implantable device in some cases mimics the anisotropic properties of the meniscus by replicating the internal microstructure which is further reinforced and covered with a coating material. In order to replicate the properties and to improve upon the field of the invention, multiple structures are employed in some embodiments to form a singular construct to replace the function of the native meniscus. The implantable device is able to mimic the localized and regional properties of the meniscus through the use of multiple structures adjoined to form a singular construct, in certain cases. Such implantable devices further resist disjointing or division into separate entities and maintain a singular structure. The implantable device is constructed from a central body sized and shaped to cover at least a portion of the tibial plateau having a top surface, a bottom surface, and a first plurality of vertical elements separating, connecting, and reinforcing the two surfaces. In some embodiments, the central body comprises a substantially crescent shape. The central body provides compressive resistance and resiliency provided by the plurality of vertical elements as well as tensile strength provided by the top surface and bottom surface and to some degree the first plurality of vertical elements. The first plurality of vertical elements are intimately connected with both the top surface and bottom surface, and provide a means to allow the central body to be resilient (i.e. return to original dimensions after loading) and to translate compressive loads into tensile forces through anchoring attachments (described in detail below as part of the third structure). Any suitable materials can be used for the vertical elements of the present invention. The top and bottom surface further feature anisotropic tensile properties which can be arranged in an orientation to mimic the circumferential and radial properties of the native meniscus with the higher tensile strength orientation in the circumferential orientation. The central body is polygonal in cross section with the top and bottom surface being relatively planar with respect to one another and forming a porous structure by the interconnecting plurality of vertical elements. The central body is curved or somewhat semi-circular in shape, that is, "substantially crescent shaped," with the internal side of the central body forming a minor arc and the external side of the central body forming a major arc. The minor arc is comprised of an internal open edge formed from the top surface and bottom surface of the central body connected by the plurality of vertical elements. The major arc is comprised of an external open edge formed from the top surface and bottom surface of the central body connected by the plurality of vertical elements. Thus, the minor arc and the major arc defined by the first plurality of vertical elements and the top surface and the bottom surface. Proceeding from the internal edge to the external edge, the central body can exhibit a gradient slope increasing in height. In some embodiments of the implantable device, the top surface and/or the bottom surface of the central body extend beyond the first plurality of vertical elements connecting the two surfaces together, thereby beyond the minor arc, the major arc, or both. The central body further comprises a narrowing in width between the minor arc and the major arc as the central body elongates distally from its central axis tapering to two elongated ends.

The implantable device further comprises a second structure, consisting of a substantially crescent shaped three-dimensional body having a first surface, a second surface, and a second plurality of vertical elements separating, connecting, and reinforcing the two surfaces often having a distance of separation less than the central body. The second structure is located adjacent to the interior minor arc of the central body. The second structure is roughly triangular (wedge-shaped) in cross section with the first surface and second surface forming a singular unified edge opposite the interior minor arc of the central body and an interconnected body with variable separation in distance increasing radially to the central body. The second structure is attached to the interior minor arc of the central body by either the top surface, bottom surface, or at least a portion of the first plurality of vertical elements proximal to the interior minor arc of the central body. As such, there is a gradient in height of the second structure from the singular unified edge to the union with the interior minor arc of the central body. In some embodiments of the implantable device, the top surface and/or the bottom surface of the central body extend beyond the first plurality of vertical elements, to connect the two surfaces together.

The second structure augments the compressive strength and resiliency provided by the first plurality of vertical elements, to a lesser degree compared to the compressive properties afforded by the central body, in some cases. In other cases, the second structure has greater compressive strength and resiliency compared to the central body. Mechanical properties of the implantable device can be tailored based on varying compressive properties and more specifically in certain instances the compressive stiffness of the second structure compared to the central body. Mechanical properties of the second structure can be further defined by the number of vertical elements included between the first surface and second surface of the second structure, the angle of insertion of the vertical elements between the surfaces of the second structure, as well as the material type and sizing with respect to the vertical elements of the central body.

The implantable device is further comprised of a third structure comprising an elongated member which is concentrically located opposite the second structure and proximal to the major arc of the central body. The third structure is comprised of an anisotropic arrangement of a plurality of filamentous elements forming a first extension and a second extension from the implantable device, in some embodiments of the present invention. The first and second extensions of the third structure are located beyond the central body and provide both a tensioning (i.e. pulling) mechanism and attachment mechanism for the implantable device in the human body. The third structure can feature a gradient change in either thickness and/or geometry. The third structure can feature a gradual decrease in thickness distally located from the central body to accommodate attachment directly to surrounding tissues and/or transosseous placement in vivo. The decrease in thickness of the third structure occurs either before or beyond the junction with the central body at the major external arc. The first and the second extensions of the third structure can also feature a change in cross-sectional geometry from either a circular, elliptical, square, rectangular, or polygonal cross-section, to a tape-like or rod-like (circular or elliptical) cross-section that can be smaller or larger in at least one dimension compared to the portion of the third structure proximal to the central body. The gradient change in thickness and/or geometry allows the third structure to act as a compressive loading surface forming the external periphery of the implantable device, as well as a means for attachment in a minimally invasive fashion afforded by the gradient transition in thickness and/or geometry. The first and second attachments also offer flexibility for placement and tensioning of the implantable device in vivo. In some embodiments the first extension and the second extension of the third structure can be comprised of the same geometry and/or thickness. In another embodiment, the first extension and the second extension of the third structure can be comprised of different geometry and/or thickness. For instance, the first extension of the third structure can be comprised of a polygonal tape-like projection while the second extension of the third structure can be comprised of a rod-like or circular projection.

The third structure features a greater stiffness compared to the central body and the second structure in both the longitudinal (tensile stiffness) and cross-sectional axis (compressive stiffness), in some cases. The third structure forms at least a portion of the peripheral rim of the implantable device. The third structure can be integrally connected with major external arc of the central body by being adjoined either to the top surface, bottom surface, or at least a portion of the plurality of vertical elements of the central body proximal to the third structure as well as any combination thereof. For example the top surface of the central body can be overlaid by the third structure and adjoined to the underlying bottom surface of the central body, enveloping and surrounding the entirety of the third structure. Moreover, the third structure is integrally attached with the major external arc of the central body such that compressive forces applied perpendicularly to the central body are converted into planar tensile forces along the third structure. In some embodiments, the third structure can be integrally attached to the central body by the first surface, the second surface, or both of the second structure which extend beyond the second structure and do not possess the plurality of vertical elements to connect to both the central body and the third structure.

The first and second extensions of the third structure may further comprise a plurality of filaments which can feature a number of configurations including but not limited to core-sheath, alternating, wedge-shaped or pie slice cross-section, interspersed, gradient, layered, among other configurations. The implantable device can further comprise at least one chemical species. The chemical species can associate with the implantable device in any suitable manner, such as, for example, being adsorbed onto or infused into the plurality of filaments of the first extension and the second extension of the third structure. That chemical species can include any suitable chemical species, such as osteogenic agents that support bone mineralization, inorganic materials, pharmacological materials, growth factors, proteins, peptides, polysaccharides, and combinations of any two or more thereof, among others. For instance, bone mineralization can be supported by preferential loading and/or delivery of inorganic materials which are capable of releasing ionic species directly from the third structure to promote bone ingrowth and permanent attachment in vivo. Ionic species which can be released from the third structure can include cationic salts such as those containing calcium ($Ca^{2+}$), zinc ($Zn^{2+}$), barium ($Ba^{2+}$), sodium ($Na^+$), magnesium ($Mg^{2+}$), or strontium ($Sr^{2+}$), or inorganic phosphates that contain ($PO_4^{-3}$). Also, silica ($SiO_2$), polyphosphates, pyrophosphates, as well as a number of proteins, peptides and pharmacological materials can be used to supplement bone mineralization. Example proteins include but are not limited to collagen, transforming growth factor β1, transforming growth factor β2, transforming growth factor β3, bone morphogenetic proteins 2, 4, 6, among others. Insoluble inorganic materials can also be included and can be chosen from hydroxyapatite, apatite, chlorapatite, fluorapatite, and hydroxylapatite.

The implantable device may further include one or more surface coatings for example positioned adjacent the top surface and/or bottom surface of the central body portion, the second structure, or a part of the third structure. Any suitable surface coating can be used. For example, one suitable surface coating comprises one or multiple layers of a lubricious substance comprised of a reinforced coating, layered underneath a non-reinforced coating. A surface coating in one embodiment comprises a reinforced lubricious coating comprising a fiber-reinforced matrix and a lubricious substance. In another embodiment, the surface coating comprises at least one reinforced layer of a lubricious substance comprising a reinforcing matrix; and at least one secondary coating, which is a non-reinforced layer of a lubricious substance, wherein the at least one secondary coating is exposed to the exterior of the implantable device. In certain instances, the reinforced lubricous coating comprises a plurality of fibrous elements not in the form of a fiber-reinforced matrix, and a lubricious substance. The surface coating can be embedded on or through the adjacent surface of the central body, the second structure, and/or the third structure. The surface coating provides enhanced lubricating and wear properties, reducing the coefficient of friction experienced during articulation, in some cases. The surface coating may further comprise a plurality of fibrous elements adapted to integrate the surface coating with the surface to which the surface coating is attached, such as a surface of the central body. The surface coating fibrous elements and reinforcing matrix can be composed of a similar chemical nature in order to promote their integration. Moreover, the coating can also be located on the second structure and the third structure of the implantable device, on one or more surfaces of those structures. The coating can be embedded on the surface or through the surface of the second structure. The coating can be embedded on or through the surface of the third structure. In some embodiments the surface coating can be present on one or more extensions of the third structure. The surface coating, in some cases, mimics the intrinsic tribological functionality of the meniscus and can be comprised of a combination of monomeric units and polymers to demonstrate this property.

Any suitable lubricious substances can be used, alone or in combination, in the embodiments of the present invention. Suitable lubricious substances include, but are not limited to, poly(ethylene glycol), poly(vinyl alcohol), poly(acrylic acid), poly(vinyl pyrrolidone), polycarbonate urethanes, segmented polyether urethanes, polyether-urethane, poly ether-urethane-urea elastomeric materials, poly(tetrafluoroethylene), silicones, and combinations thereof.

In some embodiments, the central body and the second structure can be formed from the same construct wherein the second structure is physically manipulated to form the requirements for functionality. The implantable device may further include tailorable mechanics for optimal tensile, compressive, and frictional properties.

The implantable device can be constructed from any suitable materials. In some cases, an implantable device can be constructed from a range of known materials in a film, fiber, foam, or fabric format wherein the film, fiber, foam or fabric is comprised of polyethylene, ultra-high molecular weight poly(ethylene), poly(ethylene terephthalate), poly (propylene), poly(ether urethane urea), poly(carbonate urethanes), silicones, nylons, among others. The implantable device comprises, in certain instances, a non-degradable material that has an ultimate elongation (%) of 10-2,000 percent strain with an ultimate tensile strength 30-2,000 MPa.

Also provided is an implantable device for repairing a meniscus defect or reinforcing a damaged meniscus, the implantable device including a central body having a central portion sized and shaped to cover at least a portion of the tibial plateau having an outer periphery, and a second structure having an outer periphery substantially similar to the inner periphery of the central body, and a third structure having an inner periphery substantially similar to the outer periphery of the central body. The third structure comprises at least two pulling elements coupled to the central body of the implantable device. The implantable device further includes a surface coating positioned on the first and second surfaces of the central body. Additionally, the implantable device can feature reinforcement with a porous foam of varying mechanical properties, gradients, and densities. The porous foam can be located within the central body between the top surface and the bottom surface, and/or within the second structure between the first surface and second surface, and may display orientation along the same axis or axes (axises) as any of the vertical elements in the plurality of vertical elements.

As the present disclosure explains, this may be realized through employing a three-dimensional implant that mimics the tensile, compressive, and frictional properties of the native meniscus. The three-dimensional implant features two separate yet interconnected surfaces providing the overall bulk implantable device which features a plurality of vertical elements to separate and interconnect the separate surfaces. The vertical elements provide compressive strength, resiliency, and compressive recovery and are able to feature anisotropic orientation to mimic the natural orientation and mechanics of the meniscus tissue. The three dimensional implantable device features a third structure which is comprised of a plurality of circumferential fibers connected to the two separate yet interconnected surfaces and provides a means to attach the implantable device within the human body.

BRIEF DESCRIPTION OF DRAWING FIGURES

The accompanying drawings, which are incorporated herein and form a part of the specification, illustrate some, but not the only or exclusive examples of embodiments and/or figures. It is intended that the embodiments and figures disclosed herein are to be considered illustrative rather than limiting. In the drawings.

DETAILED DESCRIPTION OF THE INVENTION

Figure 1:
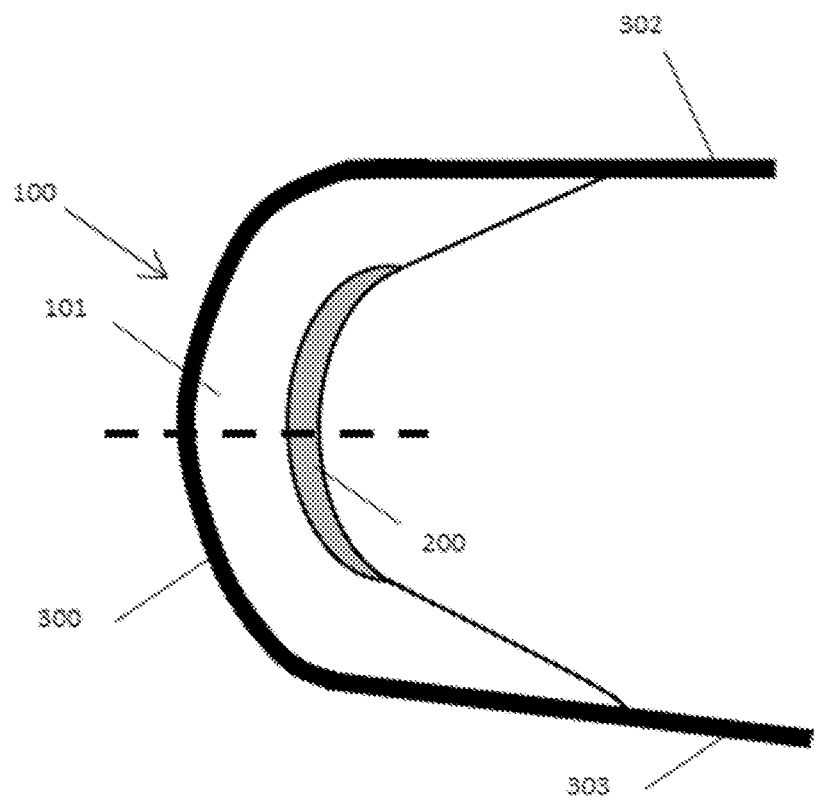
FIG. 1 is a diagrammatic top view of a first mode of the implantable device shaped to replace the knee meniscus.

Due to the limitations present within the field of the invention, at least some of the embodiments of the present invention offer significant advantages and improvements in the field. Before explaining the present invention in detail, it should be noted that the invention is not limited in its application or use to the details of construction and arrangement of parts illustrated in the accompanying drawings and description. Referring to FIGS. 1-7 certain embodiments of the present invention will now be described in detail. FIG. 1 shows implantable device 100 which is comprised of multiple structures forming a singular construct comprised of a central body 101, a second structure 200, and a third structure 300. All structures are integrally connected to form a singular construct capable of replacing a human meniscus. Methods of integrally connecting the structures can include sewing, gluing, melting, ultrasonic welding, or any other known means in the art, and combinations of any two or more of the foregoing. In this embodiment, each of these structures can be engineered to match the inherent properties of meniscus tissue based on the underlying microstructure to mimic the mechanical behavior (tensile, compressive, shear, frictional properties) as well as the geometry and size of the tissue (area, height, curvature, and slope). The implantable device is biocompatible not eliciting a harmful response to living tissue able to replace a function of the meniscus. The implantable device is non-resorbable in nature and therefore unable to undergo hydrolytic or enzymatic degradation in vivo.

In certain embodiments, the design of the structures will determine the orientation and placement position of the implantable device to replace a meniscus. The central body 101 is sized and shaped to cover at least a portion of the tibial plateau. In the illustrated embodiment, the central body 101 is substantially crescent-shaped (semi-lunar) in overall shape, having a curvature and area which is suitable for repair and/or replacement of a meniscus and able to contact at least a portion of the tibial plateau. The second structure 200 is sized and shaped to cover at least a portion of the tibial plateau and is located concentrically interior to the central body. The third structure 300 is located opposite the second structure substantially circumferentially surrounding the central body 101 and forms the periphery of the implantable device 100. The central body 101, second structure 200, and third structure 300 form at least two attachment elements called the first extension 302 and the second extension 303, which allow tension to be applied to the device 100.

Figure 2:
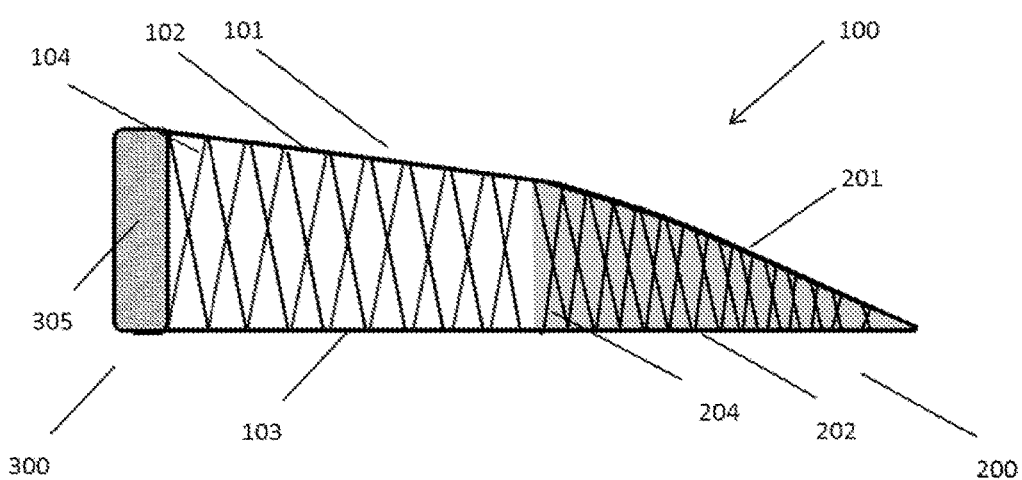
FIG. 2 is a diagrammatic side view of another mode of the implantable device employing at least three structures to replicate and mimic the compressive strength and compressive resiliency of the knee meniscus.

FIG. 2 shows a side view of the implantable device cut through the central axis, shown by a dashed line in FIG. 1. As demonstrated in FIG. 2, the central body 101 features a polygonal cross-section featuring a first set of two surfaces and a first plurality of vertical elements 104 which connect, separate, and reinforce the first set of planar surfaces further described in FIGS. 3 and 4. The first plurality of vertical elements 104 within the central body 101 can feature density dependent arrangement, varying angles of insertion into the top surface 102 and bottom surface 103 of the central body, and offer mechanical properties such as compressive resistance and resiliency. The second structure 200 features a substantially wedge-shaped cross-section where a second set of planar surfaces comprised of a first surface 201 and a second surface 202 which are connected, separated, and reinforced by a second plurality of vertical elements 204 further described in FIGS. 5 and 6. The third structure 300 features a dense arrangement of aligned filamentous elements 305 which provide a means to provide tension to the device and forms the external peripheral edge of the device 100. The third structure 300 is comprised of a polygonal body 301, first extension 302 and second extension 303 and further described in FIG. 7.

The vertical elements 104 of the central body 101 and the vertical elements 204 of the second structure 200 can be independently chosen from any suitable material. Suitable materials for vertical elements include, but are not limited to, polyesters, polyolefins, perhalogenated polyolefins such as poly(tetrafluoroethylene), polyether ether ketones (PEEK), polyurethanes, poly(carbonate urethanes) nylons, any suitable material, and combinations thereof. The vertical elements 104 of the central body 101 and the vertical elements 204 of the second structure display an aspect ratio (defined as a height to cross-sectional ratio of the vertical element) greater than ten in some cases, and greater than twenty in additional cases. The vertical elements can feature any geometry in cross-section ranging from polygonal, round, flat, oval, serrated, star, dog-bone, lobular, and any suitable shape or combination thereof.

Figure 3:
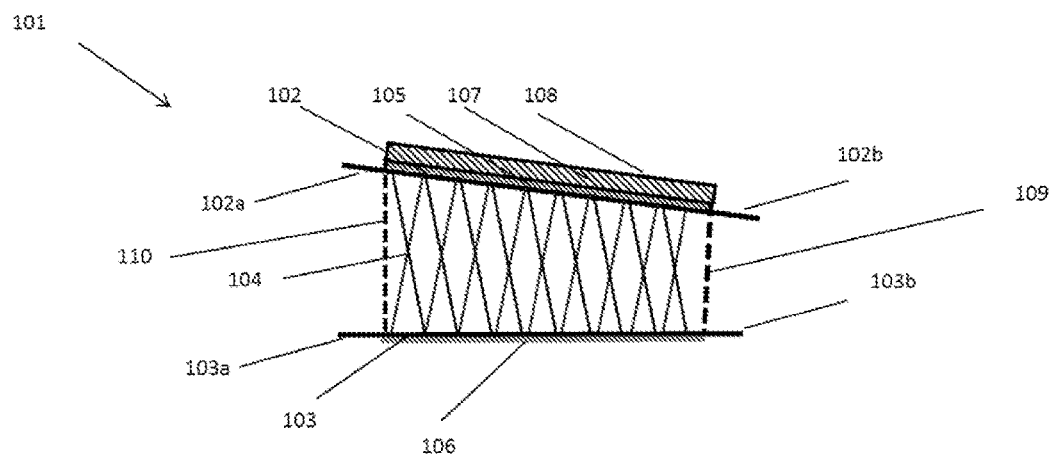
FIG. 3 is a diagrammatic side view of another mode of the implantable device employing the central body.

FIG. 3 further shows the central body 101 which includes at least two surfaces, top surface 102, and a bottom surface 103 which are separated, connected, and reinforced by a first plurality of vertical elements 104 which connect and separate the two surfaces of the central body 101. The top surface 102 and bottom surface 103 feature anisotropic tensile properties wherein the tensile strength and stiffness is greater in the long axis in the plane of the surface respective to the short axis normal to the surface. Positioned adjacent the top surface 102 and bottom surface 103 of the central body 101 are surface coatings 105 and 106, respectively. Surface coating 105 further comprises a reinforced lubricious coating 108. The reinforced lubricious coating 108 is comprised of a plurality of fibrous elements 107 inside a lubricious agent. The plurality of fibrous elements 107 are comprised of a hydro-swellable material not in the form of a fiber-reinforced matrix. Any suitable hydro-swellable material can be used, such as, for example, polyvinyl alcohols, polyethylene oxides, polycarbonate urethane copolymers with polyethers or other polymers having oxygen atoms and/or ionic groups, and combinations of two or more thereof. Each fibrous element can exhibit a fiber diameter of 0.1 μm to 20 μm in one embodiment or from 0.5 μm to 5 μm in another embodiment. The plurality of fibrous elements 107 may exhibit an areal density of 1-800 g/m$^2$ in some embodiments, and an areal density of 20-500 g/m$^2$ in other embodiments, for example. Areal density can be measured by determining the mass of the coating in grams over a known area measured in meters-squared. The plurality of fibrous elements 107 comprise poly(ethylene glycol), poly(vinyl alcohol), poly(acrylic acid), poly(vinyl pyrrolidone), polycarbonate urethanes, segmented polyether urethanes, polyether-urethane, poly ether-urethane-urea elastomeric materials, or any combination thereof. Independently of the fibrous elements 107, the lubricious substance forming the lubricious coating 108 can be chosen from any suitable material, such as, for example, poly(ethylene glycol), poly(vinyl alcohol), poly(acrylic acid), poly(vinyl pyrrolidone), polycarbonate urethanes, segmented polyether urethanes, polyether-urethane, poly ether-urethane-urea elastomeric materials, or any combination thereof. The distance from the bottom surface 103 to the top surface 102 increases from the internal edge 109 to the external edge 110 of the central body 101. In some embodiments of the implantable device, the top surface 102 and bottom surface 103 of the central body 101 extend beyond the plurality of vertical elements 104 connecting the two surfaces 102, 103 together. The extension of top surface 102 forms a deformable top surface 102a, and the extension of bottom surface forms a deformable bottom surface 103a on the external edge 110 of the central body 101 that are not connected by the plurality of vertical elements 104. In some embodiments of the implantable device 100, the top surface 102 and bottom surface 103 of the central body 101 extend beyond the plurality of vertical elements 104 on the internal edge 109 of the central body 101 forming a deformable top surface 102b and a deformable bottom surface 103b that are not connected by the plurality of vertical elements 104.

Figure 4:
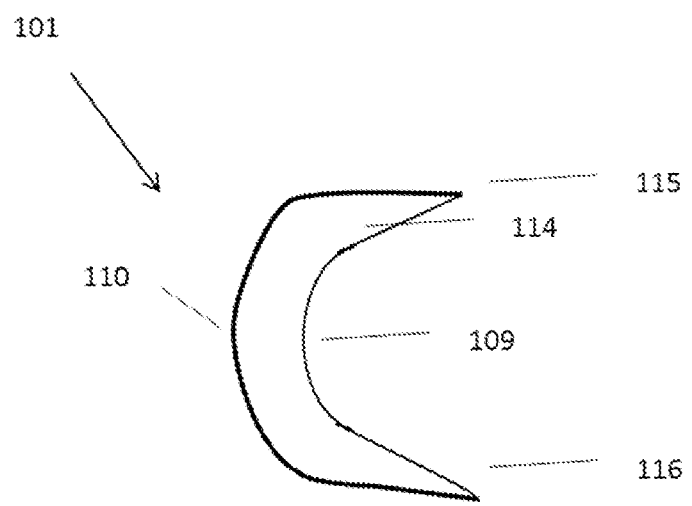
FIG. 4 is a diagrammatic top view of another mode of the implantable device employing the central body.

FIG. 4 further shows the central body 101 is substantially crescent shaped with the internal side of the central body forming a minor arc 109 and the external side of the central body forming a major arc 110. The minor arc 111 is comprised of an internal open edge formed from the top surface 102 and bottom surface 103 of the central body connected by the plurality of vertical elements 104 (see FIG. 3). The major external arc 110 is comprised of an external open edge formed from the top surface 102 and bottom surface 103 of the central body connected by the plurality of vertical elements 104. The central body further comprises a narrowing in width 114 between the minor arc 109 and the major arc 110 as the central body elongates distally from its central axis tapering to two elongated ends 115 and 116.

Figure 5:
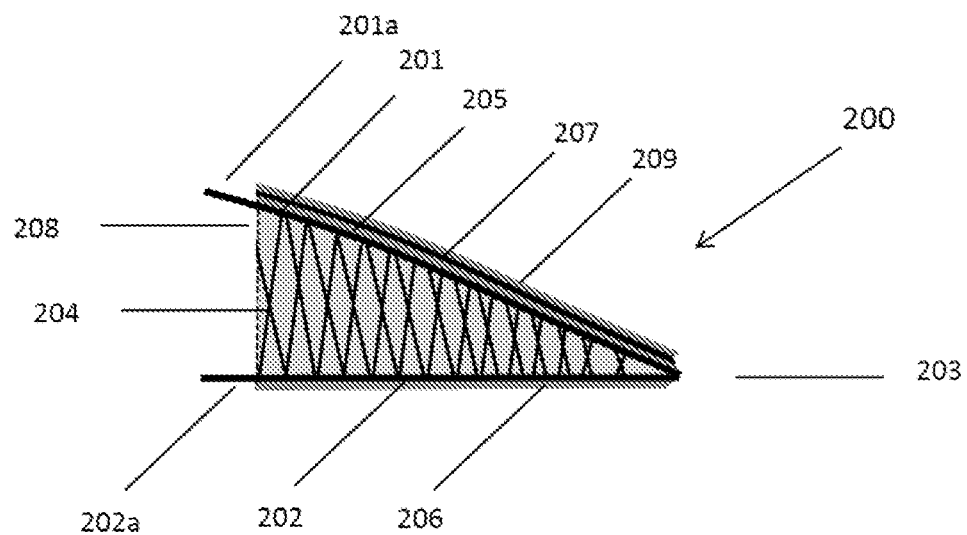
FIG. 5 is a diagrammatic side view of another mode of the implantable device employing the second structure.
Figure 6:
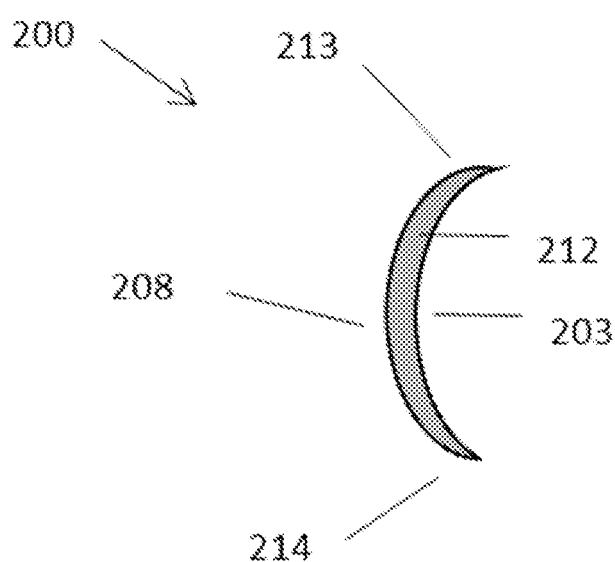
FIG. 6 is a diagrammatic top view of another mode of the implantable device employing the second structure.

Additionally, the implantable device features a second structure 200 as shown in FIG. 5, that is substantially wedge shaped in cross-section and is located interior to the central body 101 with its major external edge 208 adjacent the internal edge 109 of the central body. The second structure 200 further includes a second set of two surfaces, a first surface 201, and a second surface 202, which are connected, separated, and reinforced by a second plurality of vertical elements 204. The surfaces 201 and 202 connect and form a singular edge 203 of the second structure 200. The second plurality of vertical elements 204 allows a decrease in separation between the first surface 201 and the second surface 202 of the second structure 200. The second plurality of vertical elements 204 can be of a different strength resiliency, and/or material compared to the first plurality of vertical elements 104. The first surface 201 and the second surface 202 form a singular edge 203 opposite the major external edge 208. Additionally, the first surface 201 of the second structure 200 features a concave shape respective to the second surface 202 of the second structure 200. Positioned adjacent the first surface 201 is a surface coating comprising layers 205, 207, and 209. Positioned adjacent the second surface 202 of the second structure 200 is a surface coating 206. The layer 205 comprises poly(ethylene glycol), poly(vinyl alcohol), poly(acrylic acid), poly(vinyl pyrrolidone), polycarbonate urethanes, segmented polyether urethanes, polyether-urethane, poly ether-urethane-urea elastomeric materials, or any combination thereof. Layer 205 is adjoined by a reinforced lubricious coating being a combination of a plurality of fibrous elements 207 not in the form of a fiber-reinforced matrix with a lubricious substance, wherein the plurality of fibrous elements 207 is a semi-crystalline hydrophilic material. The reinforced coating is comprised of a plurality of fibrous elements 207 reinforced supporting a secondary coating 209. The plurality of fibrous elements 207 are comprised of a hydro-swellable material and exhibit a fiber diameter of any suitable dimension before exposure to moisture, such as, for example, from 0.1 μm to 20 μm, in some cases, and from 0.5 μm to 5 μm in other cases. The plurality of fibrous elements 207 may exhibit an areal density of 1-500 g/m$^2$ in some cases, an areal density of 20-300 g/m$^2$, in other cases, and any suitable areal density in still further cases. The plurality of fibrous elements 207 and the secondary coating 209 are independently chosen from polyethylene glycol), polyvinyl alcohol), poly(acrylic acid), polyvinyl pyrrolidone), polycarbonate urethanes, segmented polyether urethanes, polyether-urethane, poly ether-urethane-urea elastomeric materials, or any combination therein. The major external edge 208 of the second structure lies adjacent to the central body is defined by the first surface 201 and second surface 202 and the second plurality of vertical elements 204. At the major external edge 208 the first surface 201 and the second surface 202 can extend beyond the second plurality of vertical elements 204 forming a deformable first surface 201a and a deformable second surface 202a which are not connected by the second plurality of vertical elements 204. The extended deformable surfaces 201a and 202a can assist with attachment of the second structure 200 to the central body 101 and more specifically top surface 102 and bottom surface 103, respectively. As displayed in FIG. 6, the second structure 200 displays a substantially crescent or C-shape in area which features an inner edge 203 and an external arc 208. As the second structure 200 extends beyond its central axis, the width between the inner edge 203 and the external arc 208 narrows 212 to two extensions 213 and 214. Extensions 213 and 214 terminate and adjoin the elongated ends 115 and 116 of the central body 101.

Figure 7:
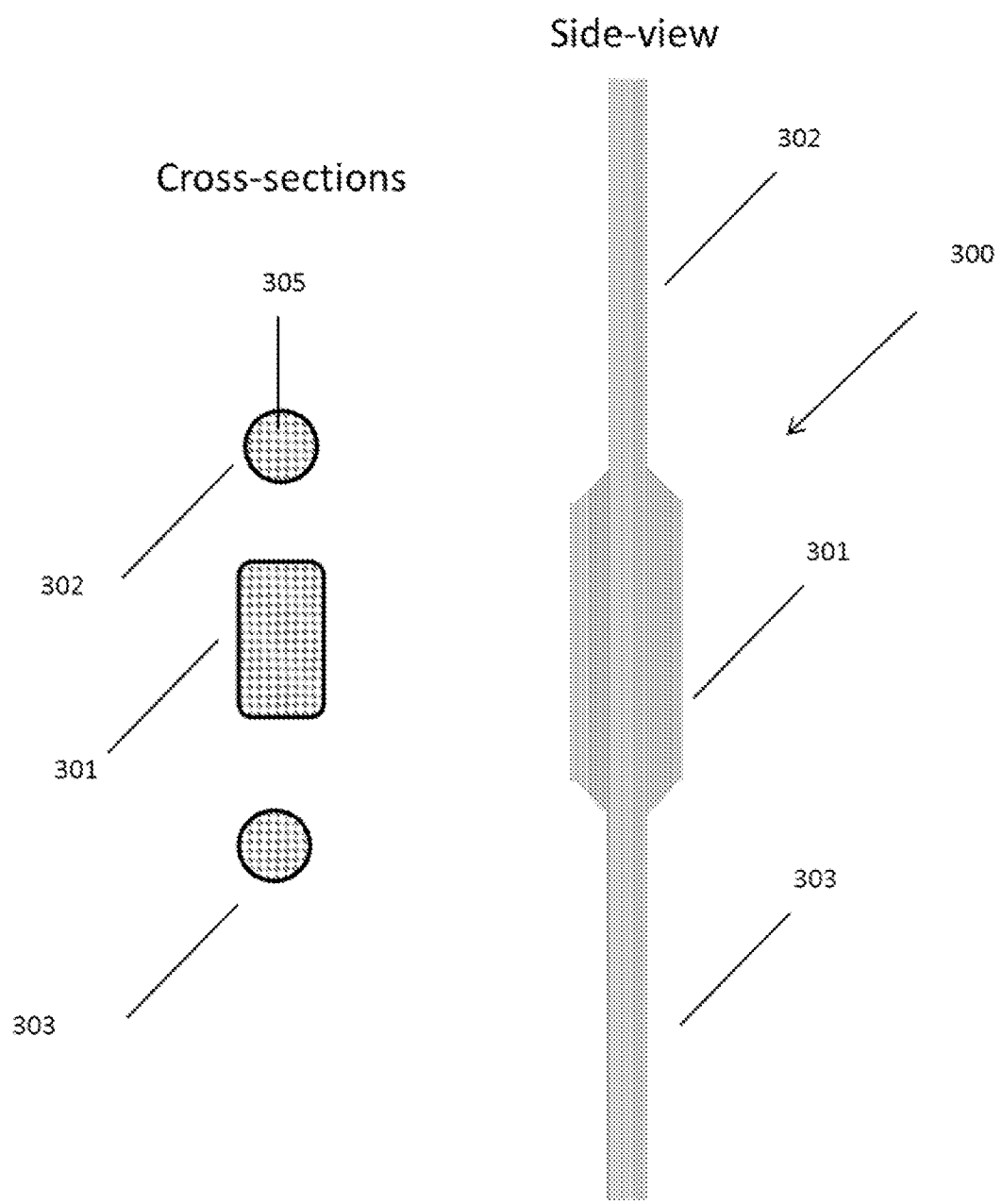
FIG. 7 is a diagrammatic side and cross-section view of another mode of the implantable device employing the third structure.

Additionally, the implantable device 100 features a third structure 300, that is adapted to conform to band be proximal to the major arc 110 of the central body 101 as shown in detail in FIGS. 1 and 2. As illustrated in FIG. 7, the third structure 300 is comprised of a plurality of filamentous elements 305 which exhibits a tensile strength greater than the central body 101 or the second structure 200. The third structure 300 is further comprised of a polygonal body 301 and first extension 302 and second extension 303 which allow the placement and attachment of the device 100 in the body. The third structure 300 is substantially circumferential to the implantable device 100 with the first extension 302 and second extension 303 extending beyond the central body 101. The extensions 302, 303 can be adjoined by the surfaces 102 and 103 of the central body connecting the central body 101 with the third structure 300, and/or with the deformable top surface 102a and a deformable bottom surface 103a on the external edge 110 of the central body 101. The third structure can also be connected to the extended surface 201a and 202a of the second structure 200. The third structure 300 features a gradient change in both geometry and size, transitioning from a polygonal cross-section 301 to circular rod-like extensions 302 and 303 distally located from the polygonal body. Additionally, extensions 302 and 303 comprise a change in size being substantially thinner than the polygonal body 301, having any suitable diameter such as, for example, a diameter of 0.1-4 mm in some cases, and of 1-3 mm in other cases, with a circular cross-section as illustrated in FIG. 7. The third structure 300 is comprised of a polymer chosen from polyesters, polyolefins, perhalogenated polyolefins such as poly(tetrafluoroethylene), polyether ether ketones (PEEK), polyurethanes, silicones, nylons, combinations of two or more thereof, and any suitable material.

The implantable device provides a means to translate compressive forces into tensile forces. This is achieved by the multiple pluralities of vertical elements which are integrated with the multiple planar surfaces of the device. As the implantable device undergoes compressive strain, the compressive force bends the plurality of vertical elements which are intimately connected with multiple planar surfaces. As the planar surfaces undergo compressive loading, the surfaces translate through towards the third structure 300 and to the attachment mechanisms first extension 302 and second extension 303. The force is translated from vertical compressive load through to tensile forces through the third structure and into the attachments. This is due to the wedge shape of the device which gives rise to a 'hoop stress mechanism' thereby reducing intra-articular contact pressures on the tibial plateau and on the femoral condyle in the knee compartment where the implantable device is located. As the device is displaced radially, the attachment retains its position and in vivo placement, resisting the displacement and giving rise to tensile strains. If the device were not wedge shaped there would be no force translation.

The attachment mechanisms first extension 302 and second extension 303 provide additional benefit for controlling placement of the implant as well a means to position the implant to the tibial plateau, tibia surface, and/or transosseosly means of attachment. During implantation and installation of the device, the surgeon can ensure a proper and congruent fit of the implant relative to the tibia plateau and femoral condyle. During this application of positioning the first extension 302 and second extension 303, the surgeon can apply tension to the attachments which will separate and expand the top and bottom surface 102 and 103 of the central body 101 of the implantable device 100. Such expansion of the implantable device 100 will allow visual conformation that the implant fills the defect and provides a congruent surface between the tibial plateau and femoral condyles. The structures of the implantable device can be comprised of a film, fabric, or plurality of fibers intermeshed by any known art in the field. To enhance and add desirable properties to the implantable device all suitable materials may possess similar tensile strength, such as around 0.5-5 GPa, but each may have significantly different tensile modulus and elongation at break, providing for property variations depending on the class of material selected.

It should also be recognized that two or more different types of materials may be used in combination to further control the final mechanical characteristics of the resulting implantable device. For example, where the materials are used for attachment upon implantation, a stronger material might be used for the third structure 300 of the implantable device, to give maximal strength to the periphery and to any anchoring attachment. Further, a substantially non-elastic material can be used to give a high level of strength along an axis, arc, or surface of an implant, while a different type of elastic and/or stretchable material might be used to provide flexibility and elastic resilience along a different axis, arc, or surface. The lubricious coating present on the central body 101 and the second structure 200 can also feature biomolecules including peptides, proteins or polysaccharides including but not limited to collagen, elastin, hyaluronan, glycosaminoglycans, among others.

In another aspect of the present invention, the structures of the implantable device may be integrated in a variety of ways, including a random or unorganized integration, or a patterned or organized integration, such as a three-dimensional mesh. In addition to the methods of manufacturing the implantable device as described herein, other methods may be used as would be understood by those skilled in the art, such as sewing, ultrasonic welding, crosslinking, gluing, weaving, braiding, knitting, knotting, nonwoven constructions, and molding. The desired shape and customized mechanical properties of the implantable device will dictate the type or combination of manufacturing techniques used.

In another aspect of the implantable device, the method for controlling the resulting mechanical properties of the implantable device is based on selective criteria for choosing suitable materials. For example, in one embodiment, the selection of material may be based on the ability to pattern the surface by using weaving, knitting, nonwoven technologies to create 2D and 3D patterns or structures. In another aspect, the selection of material may be based on the ability to create surfaces with random or directional orientation. In another aspect, the selection of material may be based on the ability to modify the surface such that they can interact with the hydrogel in which they are embedded.

As explained herein, the implantable device may be used for replacing or repairing various musculoskeletal tissues and fibrocartilage, for example in a mammal, such as the meniscus in a human. The implantable device may also be used for replacing or repairing other items, such as a secondary implant repairing or replacing a first implant. In other embodiments, the composites of the present invention can be constructed to match an allograft, or any other replacement device as would be understood by those skilled in the art.

An example of the implantable device 100 includes the central body 101 being comprised of a three-dimensional structure, wherein the top surface 102 and bottom surface 103 are comprised of two (2) knitted fabrics comprised of a poly(ethylene terephthalate) semi-dull seventy (70) denier, thirty-four (34) filament count multifilament yarn. The top surface 102 and bottom surface 103 were constructed with a tricot knit pattern or any suitable knit pattern wherein the intermeshing of the yarn forms a fabric structure. Denier refers to the linear density of the yarn and reported in grams per nine thousand meters of fiber. The top surface 102 and bottom surface 103 are further reinforced, separated, and connected by a plurality of vertical elements 104 comprised of a series of monofilament fiber of poly(ethylene terephthalate) which displays a round cross-section and diameter of 0.2 mm. The plurality of vertical elements 104 are angled into the top surface 102 and bottom surface 103 at an angle of >45°. The central body 101 is cut from bulk material to form a substantially crescent shape and annealed at about 180° C. for a duration of thirty minutes to form a polygonal cross-section wherein the internal minor arc 109 is at a lower height comparative to the external major arc 110 of the central body 101. The second structure 200 is comprised of a first surface 201 and a second surface 202 wherein the surfaces are formed from knitted construction comprised of a poly(ethylene terephthalate) one hundred thirty five (135) denier, ninety-six (96) filament count multifilament yarn which is textured. The first surface 201 and second surface 202 are constructed with an Atlas knit pattern or any suitable knit pattern wherein the intermeshing of the yarn forms a fabric structure. The first surface 201 and second surface 202 are reinforced, separated, and connected by a second plurality of vertical elements comprised of a series of monofilament fibers of poly(propylene) which displays a round cross-section and cross-sectional diameter of 0.15 mm. The second structure 200 was annealed at about 120° C. for a duration of thirty minutes to form a major edge 208 which is adjacent the internal minor arc 109 of the central body 101, wherein the second structure 200 also formed a singular edge 203 which was opposite the major edge 208. The second structure was substantially crescent shaped and triangular in cross-section. The central body 101 and second structure 200 were adjoined together be sewing with a 3-0 size ultra-high molecular weight polyethylene suture and by ultrasonic welding forming a singular construct and indiscernible structure. The third structure 300 was formed from a plurality of fibrous elements comprised of ultra-high molecular weight poly(ethylene) fibers size 3-0 and was circumferentially located around the periphery of the central body 101 and adjacent to the major external arc 110. The third structure 300 demonstrated a tensile breaking load of greater than 500 N. The third structure 300 was adjoined to the central body 101 by ultrasonic welding to the deformable top surface 102a and the deformable bottom surface 103a on the external edge 110 of the central body 101. Additionally, to promote tissue integration of the implantable device 100 and the attachment mechanisms of 302 and 303 of the third structure 300, type I collagen was solubilized under acidic conditions using 1 normal hydrochloric acid and coated onto the periphery. Coating of type I collagen occurred by dipping in solubilized type I collagen and adsorbing onto the attachment mechanisms 302 and 303. The implantable device 100 further comprised a coating which was located on the central body 101 and the second structure 200. The coating comprised electrostatically deposited fibers comprised of poly(carbonate urethane) fibers with a diameter of 2 μm and areal density of 150 g/m² reinforcing a coating comprised of poly(carbonate urethane). The electrospun fibers were electrostatically deposited onto the implantable device 100 with preferential deposition on the top surface 102 of the central body 101 and first surface 201 of the second structure 200 by dispensing poly(carbonate urethane) dissolved in a fluorinated solvent such as hexafluoroisopropanol at a concentration of 8 weight percent by volume using an electric field of 1.5 kV/cm and volumetric flow rate of 3 ml/hr through a 20 gauge capillary spinneret. The coating of poly(carbonate urethane) is dissolved in a solvent system of dimethylacetimide and tetrahydrofuran and applied by subsequent dip-coating of the implantable device 100 into the coating solution.

It should be appreciated that the implantable device may be implanted into a patient using operative techniques and procedures understood by those skilled in the art. Any suitable attachment technologies can be used, such as, for example, screws, staples, sutures, and the like to secure the first extension, the second extension, and optionally any additional attachment mechanisms to the same or different sites on the tibia, femur, patella, and fibula. In certain embodiments, medical imaging modalities can be used to define and/or model the geometry of the implantable device for implantation, thereby generating a structure and geometry that is tailored to a particular subject. Further, the operative technique used to prepare the site for implantation can be based on computer navigation and/or computer guided technology.

The methods described herein are by no means all-inclusive, and further methods to suit the specific applications as contemplated herein will be apparent to the ordinary skilled artisan.

INDUSTRIAL APPLICABILITY

Certain embodiments of the present invention are suitable for manufacture on an industrial scale.

EMBODIMENTS

Further aspects of the present invention can be understood by reference to the following embodiments.

Embodiment 1

An implantable device for repairing or replacing a knee meniscus of a human or animal patient in need thereof, comprising:
a biocompatible non-resorbable three-dimensional body, comprising:
  a central body having a substantially crescent shape and comprising a top surface and a bottom surface integrally connected, separated, and reinforced by a first plurality of vertical elements, and
  a minor arc and a major arc defined by the first plurality of vertical elements and the top surface and the bottom surface;
  a second structure having a substantially crescent shape conforming to and proximal to the minor arc of the central body, the second structure comprising a first surface and a second surface integrally connected, separated, and reinforced by a second plurality of vertical elements, and the first surface and the second surface form an inner edge distal from the minor arc of the central body;

a third structure conforming to and proximal to the major arc of the central body, substantially circumferentially surrounding the central body,
further comprising a first extension and a second extension adapted to attach the implantable device in the human or animal patient;
and
a surface coating comprising a lubricious substance and covering at least a portion of the three-dimensional body.

Embodiment 2

The implantable device according to embodiment 1, wherein the central body, second structure, and third structure form a singular construct.

Embodiment 3

The implantable device according to any one of embodiments 1-2, wherein the second structure has a substantially wedge-shaped cross-section.

Embodiment 4

The implantable device according to any one of embodiments 1-3, wherein the second structure possesses a compressive stiffness less than that of the central body.

Embodiment 5

The implantable device according to any one of embodiments 1-4, further comprising at least one attachment mechanism.

Embodiment 6

The implantable device according to any one of embodiments 1-5, exhibiting a cross-sectional geometry that differs from a cross-sectional geometry of the first extension and the second extension.

Embodiment 7

The implantable device according to any one of embodiments 1-6, wherein the top surface, bottom surface, first plurality of vertical elements, or a combination of two or more thereof comprise a polymer chosen from polyesters, polyolefins, perhalogenated polyolefins, poly(ether ether ketones), polyurethanes, silicones, nylons, and combinations of two or more thereof.

Embodiment 8

The implantable device according to any one of embodiments 1-7, wherein the first surface, second surface, second plurality of vertical elements, or a combination of two or more thereof comprise a polymer chosen from polyesters, polyolefins, perhalogenated polyolefins, polyether ether ketones, polyurethanes, silicones, nylons, and combinations of two or more thereof.

Embodiment 9

The implantable device according to any one of embodiments 1-8, wherein the third structure comprise a polymer chosen from polyesters, polyolefins, perhalogenated polyolefins, poly(ether ether ketones), polyurethanes, silicones, nylons, and combinations of two or more thereof.

Embodiment 10

The implantable device according to any one of embodiments 1-9, wherein the surface coating comprises a reinforced lubricious coating.

Embodiment 11

The implantable device of embodiment 10, wherein the reinforced lubricious coating comprises a fiber-reinforced matrix.

Embodiment 12

The implantable device according to any one of embodiments 10-11, wherein the reinforced lubricous coating comprises a plurality of fibrous elements not in the form of a fiber-reinforced matrix.

Embodiment 13

The implantable device according to any one of embodiments 10-12, wherein the reinforced lubricious coating further comprises a secondary coating.

Embodiment 14

The implantable device according to any one of embodiments 1-13, wherein the surface coating covers at least a portion of the top surface, at least a portion of the bottom surface, or both.

Embodiment 15

The implantable device according to any one of embodiments 1-14, wherein the surface coating covers at least a portion of the first surface, at least a portion of the second surface, or both.

Embodiment 16

The implantable device according to any one of embodiments 1-15, wherein the central body is proportioned to cover at least a portion of a tibial plateau of the human or animal patient.

Embodiment 17

The implantable device according to any one of embodiments 1-16, wherein the third structure exhibits greatest tensile modulus properties circumferentially around the central body.

Embodiment 18

The implantable device according to embodiment 17, wherein the third structure exhibits the lowest elastic deformation circumferentially around the central body.

Embodiment 19

The implantable device according to any one of embodiments 1-18, wherein the third structure is integrally attached to the top surface, the bottom surface, or both.

Embodiment 20

The implantable device according to any one of embodiments 1-19, wherein the third structure comprises one or more chemical species chosen from cationic salts, inorganic phosphates, polyphosphates, pyrophosphates, hydroxyapatite, apatite, chlorapatite, fluorapatite, hydroxylapatite, calcium silicate-based bioglasses, mineralizing amino acids, peptides, proteins, polysaccharides, pharmacological materials, and combinations of two or more thereof.

Embodiment 21

The implantable device according to any one of embodiments 1-20, wherein the central body and the second structure comprise at least one same material.

Embodiment 22

A method of preparing the implantable device of any one of embodiments 1-21 comprising:
obtaining the central body, the second structure, and the third structure;
affixing the second structure and the third structure to the central body to form the three-dimensional body; and
applying or forming the surface coating on at least a portion of the three-dimensional body to form the implantable device.

Embodiment 23

A method of repairing or replacing a knee meniscus of a human or animal patient in need thereof, comprising:
implanting the implantable device of any one of embodiments 1-21 into a knee of the patient.

Embodiment 24

A method of reducing the contact pressure on the articular surfaces of the tibial plateau and femoral condyle in a human or animal patient in need thereof, comprising: implanting the implantable device of any one of embodiments 1-21 between the tibial plateau and the femoral condyle of the patient.

What is claimed is:

1. An implantable device for repairing or replacing a knee meniscus of a human or animal patient in need thereof, comprising:
   a biocompatible non-resorbable three-dimensional body, comprising:
      a central body having a substantially crescent shape and comprising a top surface and a bottom surface integrally connected, separated, and reinforced by a first plurality of vertical elements, and
         a minor arc and a major arc defined by the first plurality of vertical elements and the top surface and the bottom surface;
      a second structure having a substantially crescent shape conforming to and proximal to the minor arc of the central body, the second structure comprising a first surface and a second surface integrally connected, separated, and reinforced by a second plurality of vertical elements, and the first surface and the second surface form an inner edge distal from the minor arc of the central body;
      a third structure conforming to and proximal to the major arc of the central body, substantially circumferentially surrounding the central body,
         further comprising a first extension and a second extension adapted to attach the implantable device in the human or animal patient;
   and
   a surface coating comprising a lubricious substance and covering at least a portion of the three-dimensional body.

2. The implantable device according to claim 1, wherein the central body, second structure, and third structure form a singular construct.

3. The implantable device according to claim 1, wherein the second structure has a substantially wedge-shaped cross-section.

4. The implantable device according to claim 1, wherein the second structure possesses a compressive stiffness less than that of the central body.

5. The implantable device according to claim 1, further comprising at least one attachment mechanism.

6. The implantable device according to claim 1, exhibiting a cross-sectional geometry that differs from a cross-sectional geometry of the first extension and the second extension.

7. The implantable device according to claim 1, wherein the top surface, bottom surface, first plurality of vertical elements, or a combination of two or more thereof comprise a polymer chosen from polyesters, polyolefins, perhalogenated polyolefins, polyether ether ketones, polyurethanes, silicones, nylons, and combinations of two or more thereof.

8. The implantable device according to claim 1, wherein the first surface, second surface, second plurality of vertical elements, or a combination of two or more thereof comprise a polymer chosen from polyesters, polyolefins, perhalogenated polyolefins, polyether ether ketones, polyurethanes, silicones, nylons, and combinations of two or more thereof.

9. The implantable device according to claim 1, wherein the third structure comprises a polymer chosen from polyesters, polyolefins, perhalogenated polyolefins, polyether ether ketones, polyurethanes, silicones, nylons, and combinations of two or more thereof.

10. The implantable device according to claim 1, wherein the surface coating comprises a reinforced lubricious coating.

11. The implantable device of claim 10, wherein the reinforced lubricious coating comprises a fiber-reinforced matrix.

12. The implantable device according to claim 10, wherein the reinforced lubricous coating comprises a plurality of fibrous elements not in the form of a fiber-reinforced matrix.

13. The implantable device according to claim 10, wherein the reinforced lubricious coating further comprises a secondary coating.

14. The implantable device according to claim 1, wherein the surface coating covers at least a portion of the top surface, at least a portion of the bottom surface, or both.

15. The implantable device according to claim 1, wherein the surface coating covers at least a portion of the first surface, at least a portion of the second surface, or both.

16. The implantable device according to claim 1, wherein the central body is proportioned to cover at least a portion of a tibial plateau of the human or animal patient.

17. The implantable device according to claim 1, wherein the third structure exhibits greatest tensile modulus properties circumferentially around the central body.

18. The implantable device according to claim 17, wherein the third structure exhibits the lowest elastic deformation circumferentially around the central body.

19. The implantable device according to claim 1, wherein the third structure is integrally attached to the top surface, the bottom surface, or both.

20. The implantable device according to claim 1, wherein the third structure comprises one or more chemical species chosen from cationic salts, inorganic phosphates, polyphosphates, pyrophosphates, hydroxyapatite, apatite, chlorapatite, fluorapatite, hydroxylapatite, calcium silicate-based bioglasses, mineralizing amino acids, peptides, proteins, polysaccharides, pharmacological materials, and combinations of two or more thereof.

21. The implantable device according to claim 1, wherein the central body and the second structure comprise at least one same material.

* * * * *